United States Patent [19]
Weinstein et al.

[11] Patent Number: 6,086,914
[45] Date of Patent: Jul. 11, 2000

[54] NONSEDATING FORMULATIONS FOR ALLERGIC RHINITIS WHICH POSSESS ANTIHISTAMINIC AND ANTICHOLINERGIC ACTIVITY

[76] Inventors: Robert E. Weinstein, 229 Berekely St., Boston, Mass. 02116; Allan M. Weinstein, 3301 New Mexico Ave., NW., Washington, D.C. 20016

[21] Appl. No.: 09/267,809

[22] Filed: Mar. 12, 1999

[51] Int. Cl.[7] ............................... A61K 9/14; A61K 9/20; A61K 9/48

[52] U.S. Cl. .......................... 424/451; 424/464; 424/455; 424/456; 424/489; 514/937

[58] Field of Search ..................................... 424/451, 456, 424/464, 489, 455, 452, 465

[56] References Cited

U.S. PATENT DOCUMENTS 5,116,847  5/1992  Gilbert et al. ........................... 514/327
5,661,142  8/1997  Naeger .................................... 514/178

*Primary Examiner*—James M. Spear
*Attorney, Agent, or Firm*—Hopgood, Calimafde Kalil & Judlowe

[57] ABSTRACT

It is perceived that the newer antihistamines, which have been developed so as to be less sedating relative to the "first generation" antihistamines, possess diminished anticholinergic effects on rhinorrhea, compared to first-generation antihistamines. It is also perceived that no oral medicinal formulation is presently available for treatment of allergic rhinitis that provides both antihistaminic and anticholinergic actions and is unlikely to produce sedation. This invention provides such a formulation.

6 Claims, No Drawings

NONSEDATING FORMULATIONS FOR ALLERGIC RHINITIS WHICH POSSESS ANTIHISTAMINIC AND ANTICHOLINERGIC ACTIVITY

BACKGROUND OF THE INVENTION

1. Field of the Invention

Unrelated to their function of binding to H1 histamine receptors, the first-generation antihistamines produce sedation, an unwanted side effect, but also provide anticholinergic effects, which are helpful for reducing secretions and controlling rhinorrhea. Second-generation antihistamines, which are relatively nonsedating, have been developed but are lacking in anticholinergic efficacy. Despite the abundance of presently marketed formulations for addressing the symptoms for allergic rhinitis, no medicinal formulation is presently available which provides both antihistaminic and anticholinergic actions in an essentially nonsedating manner.

2. The State of the Art

Allergic rhinitis refers to a common inflammatory condition of the nose caused by allergies and affects at least 15% of the United States population. The typical symptoms of allergic rhinitis include: sneezing, itching nose, nasal congestion and rhinorrhea ("running" or "runny" nose), often accompanied by watering and itching eyes, and post nasal drip. As related to a patient's quality of life, rhinorrhea is reported as the most prominent and distressing symptom of allergic rhinitis.

The release of histamine is an important mechanism underlying some of the symptoms of allergic rhinitis. The symptom of rhinorrhea, however, is largely attributable to a neuronal mechanism; specifically, to the effects of acetylcholine on nasal cholinergic receptors, rather than to the action of histamine. This can be demonstrated by observing that histamine challenge on one side of the nose produces an increase in nasal secretions, on the other side as well. The reflex increase in secretions on the non-challenged side can be inhibited by premedication with an anticholinergic agent, i.e., an agent which acts to blocks the action of acetylcholine on cholinergic receptors.

Two categories of medication used to treat allergic rhinitis are capable of blocking the action of acetylcholine on cholinergic neuronal receptors: (i) first-generation antihistamines, which typically inherently have anticholinergic effects, and (ii) specific anticholinergic agents.

Antihistamines of the type which antagonize H1-histamine receptors are the most frequently used medications to treat allergic rhinitis. Histamine is an important mediator released in allergic reactions, and the primary action of antihistamines relates to their ability to bind competitively to H1-histamine receptors on target organ sites, thereby blocking the ability of histamine to bind to these receptors. The first pharmaceutical entities recognized to have this property, now referred to as first-generation antihistamines, have lipophilic chemical properties, which contribute to both their sedating and their anticholinergic effects. Examples of such sedating antihistamines area brompheniramine, chlorpheniramine, diphenhydramine, promethazine, and hydroxyzine.

The sedating side effects of antihistamines have stimulated the development and marketing of non-sedating, or second-generation, antihistamines. All are less lipophilic than first-generation antihistamines, conferring a reduction in their ability to cross the blood-brain barrier and thereby cause sedation. However, these second-generation antihistamines have a concomitant diminution of anticholinergic effects and decreased potency for controlling rhinorrhea. Examples of second-generation antihistamines are: loratidine (marketed as Claritin®), fexofenadine (marketed as Allegra®), cetirizine (marketed as Zyrtec®), and astemizole (marketed as Hismanal®).

Anticholinergic agents are exemplified by the belladonna alkaloids atropine and scopolamine, which inhibit the muscarinic action of acetylcholine on structures innervated by postganglionic cholinergic nerves. These agents typically inhibit the nasal secretory mechanism and cause drying of the nasal membranes. Anticholinergic agents also are known to exert central effects which include papillary dilatation and stimulation and depression of the CNS. Attention to the central effects of the anticholinergic agent considered and the relationship of the amount of dosage to central effects are of importance in devising a non-sedating oral dosage unit for rhinitis. Drowsiness is known to occur with high doses of anticholinergic agents, and with therapeutic doses of oral scopolamine, but drowsiness is considered rare with therapeutic doses of other oral anticholinergic agents (USPDI Drug Information for the Health Care Professional, 16th Edition, United States Pharmacopoeia Convention, Inc., 219–235, 1996 Rand McNally, Taunton, Mass.). Further, anticholinergic pharmaceuticals have been developed which have a limited capacity to pass across lipid membranes, such as the blood-brain barrier, and therefore have a limited capacity to produce central effects. Examples of these agents are the quaternary ammonium compounds methscopolamine and glycopyrrolate.

A multitude of medications are presently marketed and indicated for treating the symptoms of allergic rhinitis. None however, provides antihistaminic activity, anticholinergic activity, and a low potential for sedation. Some of the presently marketed formulations do contain both an antihistamine and an anticholinergic agent, but all are sedating by virtue of including a sedating antihistamine, and some are sedating because of the sedating anticholinergic agent scopolamine. Examples of these are:

1. Dura-vent DAS Tablets, which contains: phenylepherine 30 mg; chlorpheniramine 8 mg; and methscopolamine nitrate 3.5 mg. The first-generation antihistamine, chlorpheniramine, is sedating.

2. Atrohist® Plus, which contains: phenylepherine hydrochloride 25 mg, phenylepherine 50 mg, chlorpheniramine 8 mg, and hyoscyamine sulfate 0.19 mg; atropine sulfate 0.04 mg, and scopolamine hydrobromide 0.01 mg, and has the potential for sedation by virtue of the incorporation of the sedating antihistamine, chlorpheniramine, and the sedating anticholinergic agent scopolamine.

No oral medicinal formulation is presently available to a user which provides both antihistaminic and anticholinergic actions in a manner unlikely to produce sedation, despite the prevalence of allergic rhinitis and patients seeking attention for its treatment.

SUMMARY OF THE INVENTION

In summary, this invention provides oral medicinal formulations comprising an antihistaminic component and an anticholinergic component wherein said formulations are essentially nonsedating. The invention also provides a method for treating allergic rhinitis and similar conditions by providing an oral formulation comprising an antihistaminic agent and an anticholinergic agent which, in combination, are essentially nonsedating, and orally administering said formulation to a patient in need thereof.

The frequent need for treatment, and the multitude of antihistaminic medications which make concession to either sedation of rhinorrhea, underscores the present need for the formulations of this invention.

DETAILED DESCRIPTION OF THE INVENTION

Second-generation antihistamines are frequently prescribed in preference to first-generation antihistamines in order to avoid sedation, despite their lack of anticholinergic effect. The formulation of an anticholinergic agent together with a non-sedating antihistamine would "reinstate" the anticholinergic effects which have been lost in the transition from first-generation to second-generation antihistamines. It is therefore an object of the present invention to devise oral antihistaminic formulations for allergic rhinitis that are non-sedating in comparison to the sedation accompanying older antihistamines, but which still confer the anticholinergic properties forfeited by the newer non-sedating antihistamines. As used in the claims, the term "essentially non-sedating" means that the majority of people using a particular pharmaceutical agent or formulation of agents do not experience sedative side-effects; while there are always variations on side-effects of pharmaceutical agents within a given population, in this case what is intended is that an essentially nonsedating formulation is one with limited capacity to produce sedating effects in comparison with first-generation antihistamines. The inventive dosage formulations contain at least an antihistamine which is relatively lacking in sedative potential and anticholinergic properties in comparison to first-generation antihistamines, and an anticholinergic agent. The preferred type of anticholinergic agents include those which are limited in sedative potential at dosage levels which inhibit the nasal secretory mechanism so as to dry nasal secretions.

The following are examples of proposed non-sedating antihistamine formulations that restore the anticholinergic action forfeited by second-generation antihistamines. Formulations may incorporate timed release delivery of individual or all ingredients to achieve a desired dosing regimen, as is known in the art.

- loratidine 5 mg and methscopolamine nitrate 2.5 mg (the latter time-released over 12 hours) to be taken every 12 hours.
- fexofenadine hydrochloride 60 mg and glycopyrrolate 2 mg to be taken every 12 hours.
- loratidine 5 mg and glycopyrrolate 2 mg to be taken every 12 hours.
- fexofenadine hydrochloride 60 mg and atropine sulfate 0.5 mg (the latter time-released over 12 hours) to be taken every 12 hours.
- loratidine 5 mg and atropine sulfate 0.5 mg (the latter time-released over 12 hours) to be taken every 12 hours.
- cetirizine hydrochloride 10 rag, and methscopolamine nitrate 5 mg (the latter time-released over 24 hours) to be taken once per day.

Other formulations which restore the anticholinergic action forfeited by second-generation antihistamines are within the scope of the present invention. Such formulations may include non-sedating antihistamines and anticholinergic agents yet to be developed. The incorporation of agents to achieve additional therapeutic effects, such as medication primarily to decongest nasal passages, or agents which produce inhibition of mechanisms involved in allergic rhinitis other than the histamine mechanism, also are within the scope of this invention. In its preferred embodiment, the described formulations are provided as single oral dosage units in such forms as tablets, capsules, gel caps, powders, or in bulk liquid forms, such as syrups, as is conventionally known, and further may contain conventional materials as known in pharmaceutical formulation practice as appropriate binding agents, gellants, fillers, tabletting lubricants, surfactants, flavorings, and colorants, materials to effect desired absorption rate, bioavailability, and the like.

Various modification and alteration of the present invention may be appreciated based on a review of this disclosure, and such changes and additions are intended to be within the scope and spirit of this invention as defined by the following claims.

What is claimed:

1. An essentially non-sedating oral medicinal formulation consisting essentially of: an antihistaminic agent which is limited in both sedating and anticholinergic properties in relation to sedating first-generation antihistamines, and an anticholinergic agent.

2. The dosage unit of claim 1, wherein the medicinal formulation is in the form of a tablet, capsule, gellcap, powder, or a liquid.

3. A method of treating allergic rhinitis in a patient suffering therefrom, said method comprising: (i) providing an essentially non-sedating oral medicinal formulation consisting essentially of (a) an antihistaminic agent limited in both sedating and anticholinergic properties in comparison with sedating first-generation antihistamines, and (b) an anticholinergic agent, and (ii) administering said formulation to said patient in need thereof.

4. The method of claim 3, wherein the medicinal formulation is in the form of a tablet, capsule, gellcap, powder, or a liquid.

5. An essentially non-sedating oral medicinal formulation consisting essentially of: an antihistaminic agent which is limited in both sedating and anticholinergic properties in relation to sedating first-generation antihistamines, an anticholinergic agent, and a nasal decongestant.

6. A method of treating allergic rhinitis in a patient suffering therefrom, said method comprising: (i) providing an essentially non-sedating oral medicinal formulation consisting essentially of: (a) an antihistaminic agent limited in both sedating and anticholinergic properties in comparison with sedating first-generation antihistamines, (b) an anticholinergic agent, and (c) a nasal decongestant, and (ii) administering said formulation to said patient in need thereof.

\* \* \* \* \*